United States Patent [19]

Banes

[11] Patent Number: 6,037,141

[45] Date of Patent: Mar. 14, 2000

[54] CULTURE COMPRESSION DEVICE

[76] Inventor: Albert J. Banes, 1821 Coleman Loop Rd., Hillsborough, N.C. 27278

[21] Appl. No.: 09/326,396

[22] Filed: Jun. 4, 1999

Related U.S. Application Data

[60] Provisional application No. 60/087,915, Jun. 4, 1998.

[51] Int. Cl.[7] ............................................... C12Q 1/24
[52] U.S. Cl. .................... 435/30; 435/286.6; 435/288.3; 435/288.4; 435/305.3; 435/305.1
[58] Field of Search .................................. 435/395, 401, 435/420, 286.6, 287.1, 288.3, 288.4, 289.1, 305.1, 305.2, 305.3, 305.4, 1.1, 29, 30; 73/760, 788, 794, 795, 796, 797, 818, 819, 831, 849, 856

[56] References Cited

U.S. PATENT DOCUMENTS

| | | | |
|---|---|---|---|
| 4,087,327 | 5/1978 | Feder et al. | 195/1.7 |
| 4,623,355 | 11/1986 | Sawruk | 623/66 |
| 4,642,220 | 2/1987 | Björkman | 422/101 |
| 4,695,547 | 9/1987 | Hilliard et al. | 435/173 |
| 4,735,778 | 4/1988 | Maruyama et al. | 422/102 |
| 4,839,280 | 6/1989 | Banes | 435/285 |
| 4,940,853 | 7/1990 | Vandenburgh | 435/240.23 |
| 5,348,879 | 9/1994 | Shapiro et al. | |

FOREIGN PATENT DOCUMENTS 2155948  10/1985  United Kingdom ............. C12M 1/18

OTHER PUBLICATIONS

Leung et al., "Cyclic Stretching Stimulates Synthesis of Matrix Components by Arterial Smooth Muscle Cells in vitro", Science, vol. 191, Feb. 6, 1976, pp. 475–477.

Brunette, "Mechanical Stretching Increases the Number of Epithelial Cells Synthesizing DNA in Culture", J. Cell Sci. 69, 35–45 (1984).

Somjen et al., "Bone Remodelling Induced by Physical Stress is Prostaglandin $E_2$ Mediated", Biochimica et Biophysica Acta, 627 (1980) 91–100.

Banes et al., "A New Vacuum–Operated Stress–Providing Instrument That Applies Static or Variable Duration Cyclic Tension or Compression to Cells In Vitro", J. Cell Sci. 75 (1985) pp. 1–8.

Leung et al., "A New In Vitro System for Studying Cell Response to Mechanical Stimulation", Exp. Cell Res. 109 (1977), pp. 285–298.

Winston et al., "The In Vitro Response of Endothelium to Mechanical Loading", 38th ACEMB 1985, p. 88.

Winston et al., "Response of Endothelial Cells in Culture to Biaxial Deformation", Northeast Bioengineering Conference, University of Pennsylvania, 1987, 2 pp.

Thibault et al., "Mechanical Characterization of Membrane-like Biological Tissue", J. Biomechanical Engr., 1982, pp. 1–8.

*Primary Examiner*—David A. Redding
*Attorney, Agent, or Firm*—Webb Ziesenheim Logsdon Orkin & Hanson, P.C.

[57] ABSTRACT

A culture compression device including an enclosure having a wall and a base made from a flexible membrane. A sample support member is positioned on the membrane and retains a cell culture thereon. A stop member is mounted on top of the wall in overlying spaced apart relationship to the cell culture support. When the membrane flexes towards the stop member, the cell culture is compressed against the stop member.

27 Claims, 9 Drawing Sheets

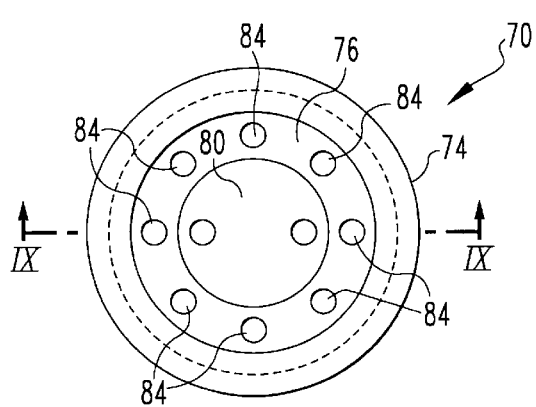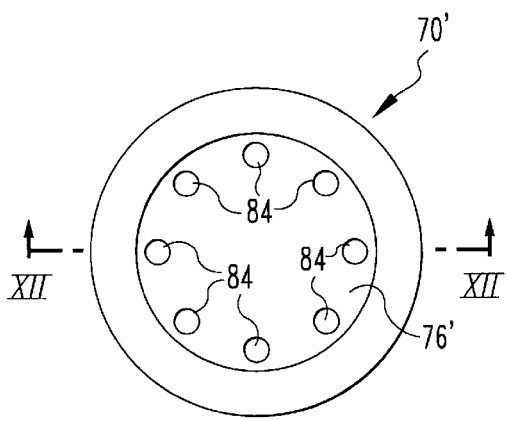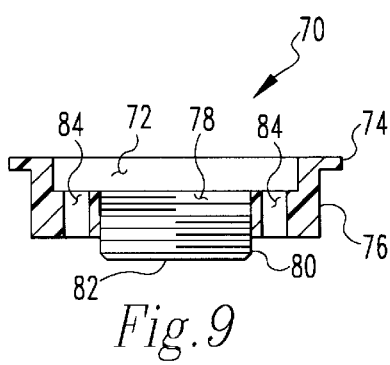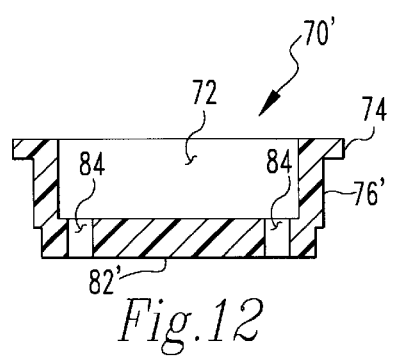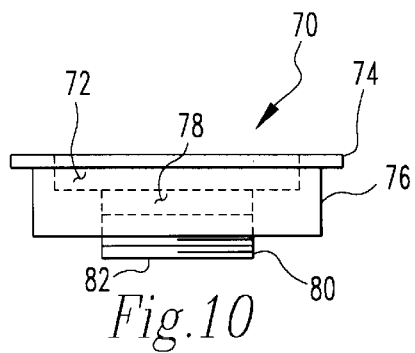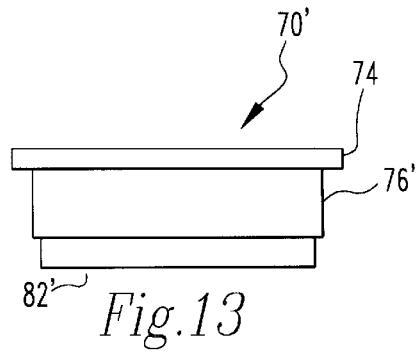

CULTURE COMPRESSION DEVICE

RELATED APPLICATION

This application claims the benefit of U.S. Provisional Application Ser. No. 60/087,915, filed Jun. 4, 1998, entitled "Culture Compression Device".

BACKGROUND OF THE INVENTION

1. Field of the Invention

The present invention relates to a device for inducing compression in a cell culture, more particularly, to a sample support which is fixed to a flexible membrane, where, upon movement of the flexible membrane, the sample support is compressed against a stop thereby compressing a cell culture retained on the support.

2. Prior Art

Culturing cells in vitro for subsequent implantation in a patient is an emerging area in medicine. Presently, cells such as cartilage cells are cultured by removing a piece of articular cartilage from a healthy section of the knee, isolating chondrocytes, increasing the number of chondrocytes in culture and implanting the cells into a defect in a patient's cartilage. A drawback to this method of implanting cultured cells into a patient's cartilage is that the cartilage that forms in vivo has less than 30% of the biomechanical strength of normal cartilage cells.

Therefore, a need has arisen to develop a device for culturing cells in vitro including cartilage tissue that can yield cells and a matrix which have sufficient material strength to withstand rigorous use in joints such as the knee or other biomechanically active environments that subject cells to compressive loads. Present tissue engineering techniques so far have been unable to produce such cells and matrix which can withstand compressive loads. For example, one method that has been used to cultivate cartilage cells in an environment to simulate the native dynamic state of repeated compressive loads is to culture the cells within a metal cylinder. A metal piston received within the cylinder is driven to induce a compressive load upon the cells during culturing in confined or unconfined compression. However, this method of using metallic piston in cylinder components to provide compression to cells and tissues grown in vitro still does not sufficiently mimic the native environment. The volume of the bathing medium is usually insufficient to sustain cells for a long period, there is difficulty in adding or removing medium and it is difficult to optically examine the sample during dynamic compression. Hence, the cells cultured thereby do not possess the required biomechanical strength of native tissue.

Another approach to applying compressive loads to cartilage is that of applying hydraulic pressure to cells or tissue confined in a tube. A nutrative medium is pumped into a three-dimensional construct populated with cells that is confined in a tube or cylinder in line with the pump. The flowing medium provides nutrition, but also adds fluid sheer stress as well as compression to the matrix and cells. However, the upstream fluid flow side of the sample will be subjected to greater pressure than the downstream side. Hence, a non-hydrogenous pressure gradient will occur throughout the sample. There is also difficulty in sustaining flow through the sample as cells divide, produce a matrix and fill in the interstices of the support matrix. Eventually, the fluid pressure will of necessity be quite high in order to provide nutrition to cells. In this case, cell death may occur due to excessive pressure. At this point, diffusion may be the principle means by which nutrition is provided to cells in the three-dimensional matrix.

Accordingly, a need remains for a device which cultures cells under compressive loads either for implant into a patient and/or for studying the impact of compressive load placement upon cell cultures, is user friendly, easily sterilized, allows for ease of sample loading, mechanical loading, addition and removal of nutrifying medium, addition of bioactive agents and allows viewing of the samples.

SUMMARY OF THE INVENTION

This need is met by the cell culture compression assembly of the present invention which includes (i) an enclosure comprising a wall and a base, wherein the base includes a flexible membrane; (ii) a sample support member positioned on the membrane; and (iii) a stop member mounted on the wall in overlying spaced apart relationship to the sample support member. The membrane is configured to flex towards the stop member thereby compressing the sample support member against the stop member.

The stop member has a flange surrounding a main portion, and the flange is seated on the wall. The position of a lower surface of the main portion may be adjustable or fixed. Preferably, the main portion defines a hole and further includes an insert bearing the lower surface and which is movable through said hole. The insert may be threadable into the hole. The main portion of the stop member defines a plurality of apertures, whereby when the membrane flexes towards the stop member, fluid present in the enclosure between the membrane and the stop member flows out of the enclosure through the apertures.

Preferably, the main portion of the stop member and the sample support member are made from a transparent material so that cells cultured on the support member are visible from the top of the assembly.

The sample support member comprises a body and a retaining member fixed to a surface of the body. The retaining member defines an opening. A sample holder is removably positioned within the retaining member opening and includes a cell culture sheet and a holder body fixed to one side of the sheet. The holder body defines at least one sample chamber. Preferably, the retaining member and the holder body are ring-shaped. Alternatively, the holder body may be disk-shaped and define a plurality of sample chambers therein. During flexing of the membrane, the retaining member is compressible to a height of about five millimeters above the surface of the support body. The sample may be a cell pellet, cells in a gel matrix, cells in a synthetic or biosynthetic matrix or cells in native tissue. However, the geometry of the cell-tissue construct should be uniform to avoid stress shielding during compressive loading.

The present invention further includes a cell culture compression assembly including: (i) a cell culture plate defining an opening and having a flexible membrane covering the opening; (ii) a sample support member positioned on the membrane; and (iii) a stop member positioned in overlying spaced apart relationship to the sample support member. The membrane is configured to flex towards the stop member, thereby compressing the sample support member against the stop member. The cell culture plate includes a wall surrounding the membrane thereby defining a cell culture well, and the stop member includes a flange portion and a main portion, the flange portion being seated on said wall and the stop member main portion extending into the well. The main portion of the stop member includes a lower surface, wherein a position of the lower surface is adjustable. The assembly further includes means for clamping the stop members against the walls.

Preferably, the cell culture plate defines a plurality of openings, with each of the openings being covered by the flexible membrane and being surrounded by a wall thereby defining a plurality of cell culture wells. A stop member is seated on one or more of the walls. The main portion of the stop member may be made from a transparent material such that cells in a matrix present on the sample support member are visible through the main portion.

In an alternative embodiment, the main portion defines an opening and the stop member includes a transparent member covering the main portion opening such that cells or a cell matrix are visible through the main portion opening. The wall includes a lower member and an upper member with the membrane being fixed between the lower member and the upper member and the flange portion of the stop member being fixed to the upper member.

The present invention further includes a method of applying compressive forces to cultured cells with steps of: a) providing a flexible membrane; b) positioning a sample support member containing a cell culture on the flexible membrane; c) positioning a stop member in overlying spaced apart relationship to the sample support member; and d) flexing the membrane in the direction of the stop member thereby compressing the cell culture against the stop member. The method may further include the steps of: e) allowing the membrane to relax and f) repeating steps d) and e). Preferably, the sample support member used in the method of the present invention includes a body and a retaining member fixed to one side of the body, such that the retaining member contains the cell culture containing cells or a cell matrix sample, and wherein the step of flexing the membrane compresses the retaining member to a height of about five millimeters above the surface of the body. The membrane preferably is incorporated into a cell culture plate defining an opening with the membrane covering the cell opening, the opening surrounded by a wall thereby defining a well, and wherein the stop member is positioned on the wall. The stop member extends into the well at an adjustable distance, such that the pressure exerted on the cell culture during the step of flexing the membrane is variable.

A complete understanding of the invention will be obtained from the following description when taken in connection with the accompanying drawing figures wherein like reference characters identify like parts throughout.

BRIEF DESCRIPTION OF THE DRAWINGS

FIG. 8 is a plan view of the stop member shown in FIG. 1;

FIG. 9 is a cross-section taken along lines IX—IX in FIG. 8;

FIG. 10 is a side view of the stop member shown in FIG. 8;

FIG. 11 is a plan view of another embodiment of the stop member;

FIG. 12 is a cross-section taken along lines XII—XII in FIG. 11;

FIG. 13 is a side view of the stop member shown in FIG. 11;

DESCRIPTION OF THE PREFERRED EMBODIMENTS

Figure 1:
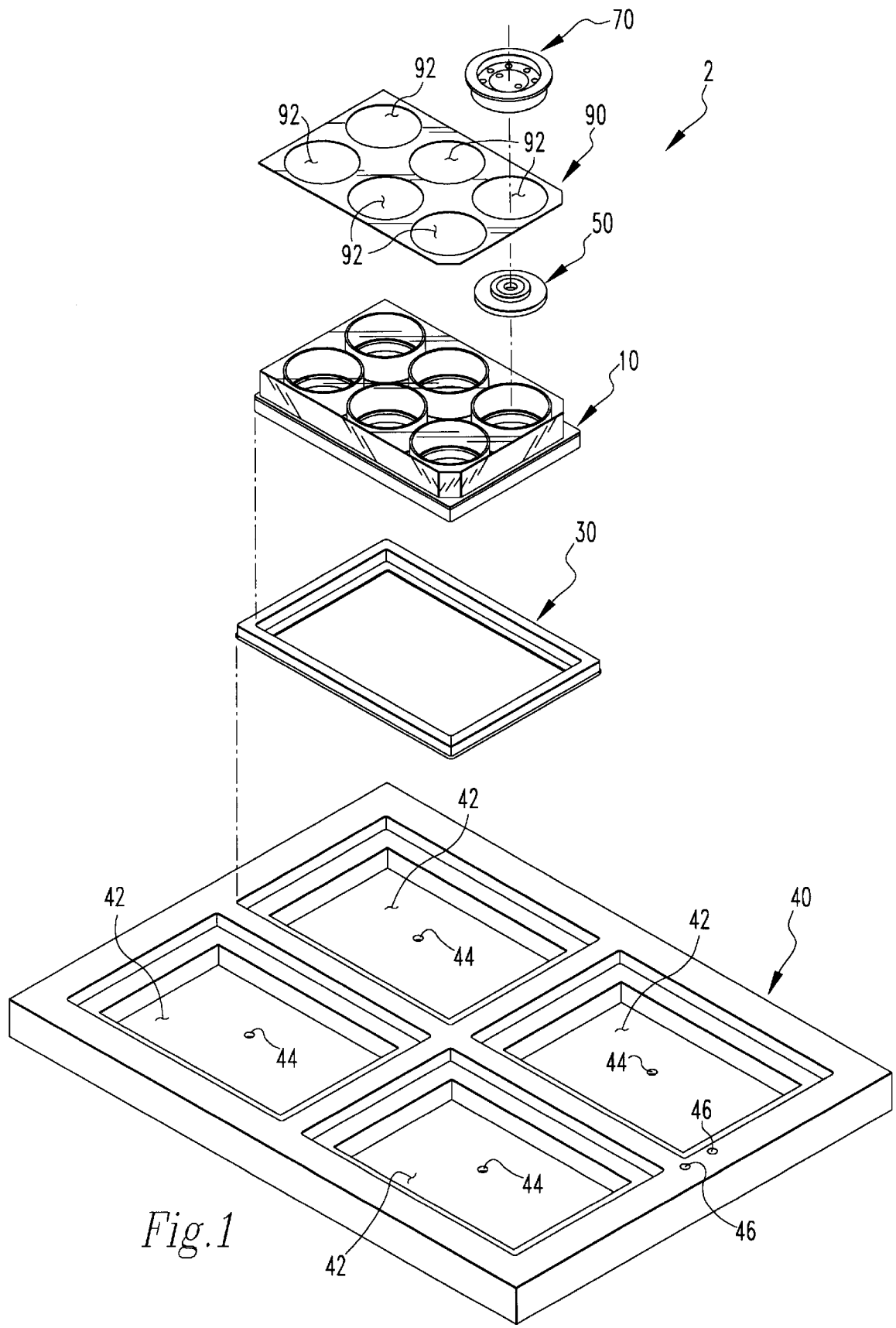
FIG. 1 is an exploded perspective view of a cell culture compression assembly incorporating a stop member, a sample support member, and a cell culture plate with a membrane made in accordance with the present invention in use with a shim, a gasket, and a cell culture base plate.

For purposes of the description hereinafter, the terms "upper", "lower", "right", "left", "vertical", "horizontal", "top", "bottom" and derivatives thereof shall relate to the invention as it is oriented in the drawing figures. However, it is to be understood that the invention may assume various alternative variations and step sequences, except where expressly specified to the contrary. It is also to be understood that the specific devices and processes illustrated in the attached drawings, and described in the following specification, are simply exemplary embodiments of the invention. Hence, specific dimensions and other physical characteristics related to the embodiments disclosed herein are not to be considered as limiting.

The cell culture compression assembly of the present invention is described as incorporating a cell culture plate wherein the floors of the wells are formed from a flexible material. Suitable multi-well cell culture plates are shown in commonly owned U.S. Pat. No. 4,789,601 and U.S. patent application Ser. No. 09/201,570 filed Nov. 30, 1998, both incorporated herein by reference. For convenience, the cell culture compression assembly is described hereinafter as used with the devices disclosed in the '570 application, but this is only meant to be exemplary. It should be understood that the cell culture compression assembly may be used with other cell culture enclosures having flexible bottoms which are not specifically described herein. In addition, the cell culture pressure assembly may also be used with single-well enclosures.

In its most basic form, the present invention includes a cell culture enclosure having a base formed from a flexible membrane, a sample support member configured to retain cells and which is fixed to the membrane, and a stop member against which the sample support member compresses when the membrane flexes towards the stop member.

Figure 2:
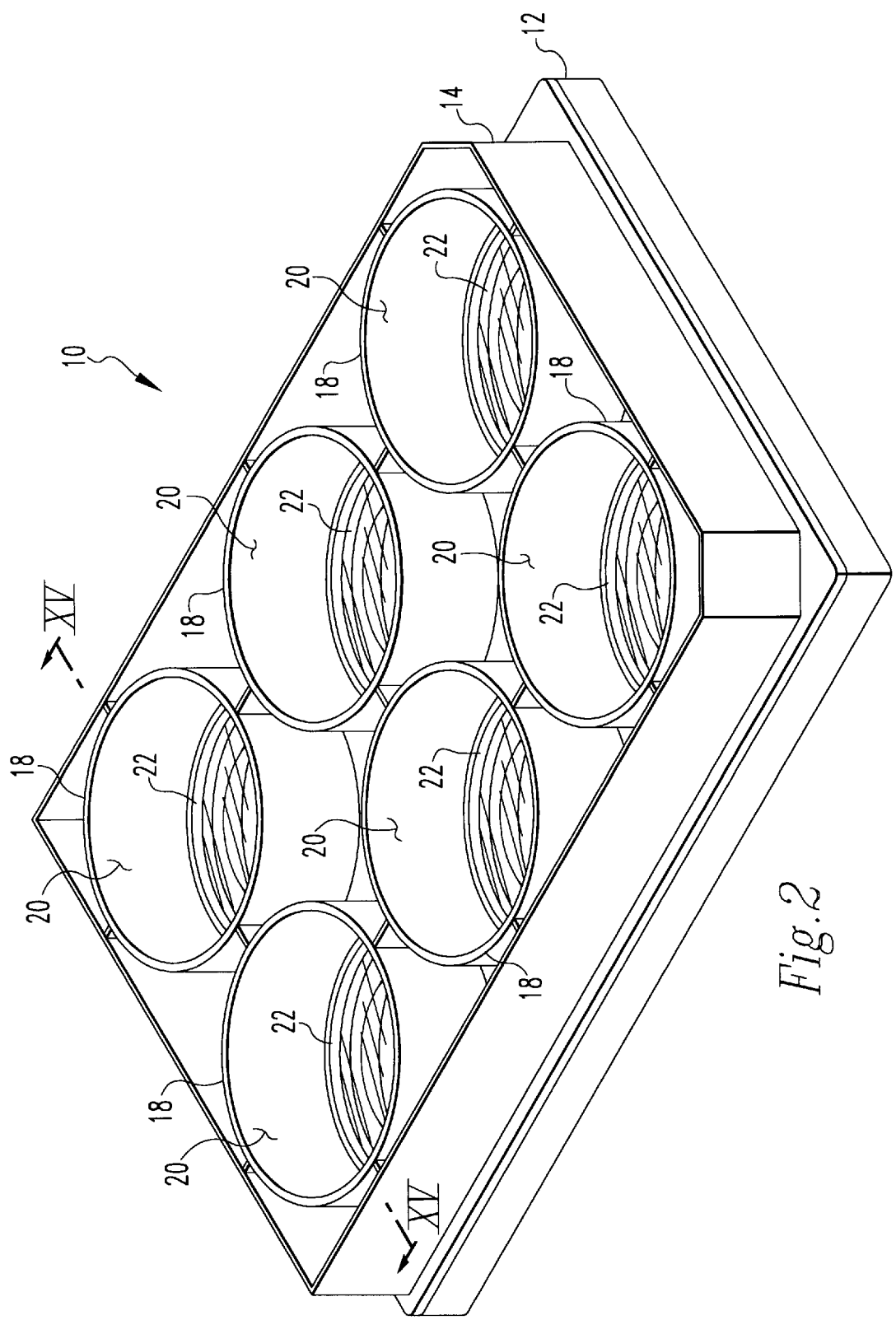
FIG. 2 is a perspective view of the cell culture plate shown in FIG. 1.

As shown in FIGS. 1 and 2, one embodiment of the cell culture compression assembly 2 of the present invention includes a multi-well cell culture enclosure or plate 10 similar to the cell culture plate disclosed in the '570 application which is fitted into a gasket 30 receivable within a cell culture base plate 40. The culture plate 10 includes a base 12, a body 14, and a flexible membrane 16 sandwiched therebetween. The body 14 includes a plurality of walls 18 which define wells 20. Floors 22 of the wells 20 are formed from the flexible membrane 16.

The cell culture compression assembly 2 includes a sample support member 50 sized and configured to be positioned onto an upper surface of the floors 22 of the wells 20. The cell culture compression assembly 2 further includes a stop member 70 sized and configured to fit within the wells 20 of the cell culture plate 10 and overlie the sample support member 50 in a spaced apart relationship. FIG. 1 shows a single sample support member 50 and a single stop member 70 with one cell culture plate 10. However, a sample support member 50 and a stop member 70 may be positioned in each well 20 of the cell culture plate 10.

Figure 5:
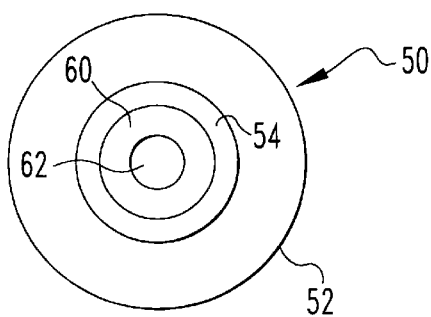
FIG. 5 is a plan view of the sample support member shown in FIG. 3.
Figure 3:
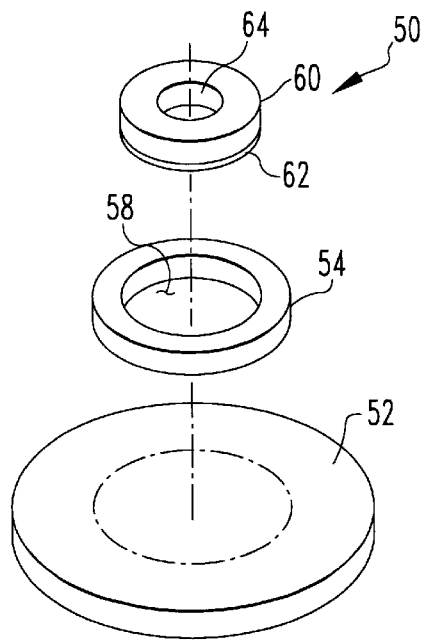
FIG. 3 is an exploded perspective view of the sample support member shown in FIG. 1.
Figure 4:
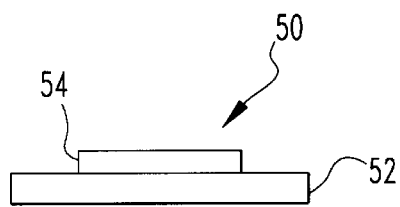
FIG. 4 is a side elevation view of the sample support member shown in FIG. 3.

Referring to FIGS. 3–5, the sample support member 50 includes a body 52 and a retaining member 54 fixed via an adhesive to an upper surface of the body 52. A lower surface of the body 52 is covered with an adhesive to fix the body 52 to the membrane 16 of the cell culture plate 10. Preferably, the body 52 is disk-shaped and is formed from transparent acrylic. The retaining member 54 preferably is formed in a ring shape from open cell low-density polyester foam and defines a central opening 58. A sample holder 60 is removably positioned within the central opening 58 of the retaining member 54. A cell culture sheet 62 is fixed to a lower surface of the sample holder 60 via an adhesive. The cell culture sheet 62 preferably is a disk formed from polyvinyl chloride about 0.003 inch in thickness. The sample holder 60 is preferably ring-shaped with an outer surface which mates with the inside surface of the ring-shaped retaining member 54. A central opening 64 defined in the sample holder is aligned with the central opening 58 of the retaining member 54 and, along with the cell culture sheet 62, serves as a sample chamber. The sample holder 60 and cell culture sheet 62 may be used to culture cells at a location remote from the cell culture compression assembly 2 for subsequent use in the assembly 2.

Figure 6:
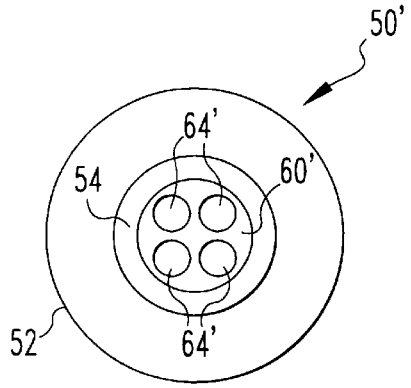
FIG. 6 is a plan view of another embodiment of the sample support member.
Figure 7:
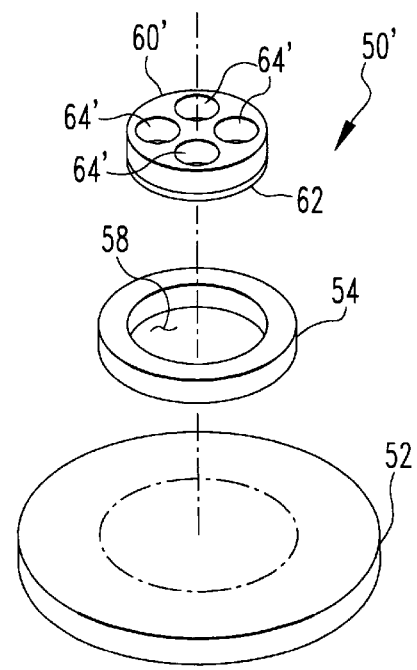
FIG. 7 is an exploded perspective view of the sample support member shown in FIG. 6.

An alternative sample support member 50' with a sample holder 60' is shown in FIGS. 6 and 7. The sample holder 60' includes a plurality of, preferably four, openings 64'. Each opening 64', along with the cell culture sheet 62, defines a sample chamber. In this manner, different types of cultures, including cells, tissues or cell-populated constructs, can be placed in a single sample chamber of the sample holder 60'. Preferably, the sample holders 60 and 60' are up to about two centimeters in diameter and up to about one centimeter high, more preferably, about four millimeters in diameter and about four millimeters high.

Referring to FIGS. 8–10, the stop member 70 is preferably cylindrical in overall shape and defines a recess 72 surrounded by a flange 74 integrally formed with a main portion 76. The main portion 76 defines a threaded hole 78 into which an insert 80 is threaded. The insert 80 includes a lower surface 82 against which a sample of a cell culture may be compressed as described below. The location of the lower surface 82 of the insert 80 is adjustable by threading the insert 80 into or out of the hole 78 to a desired position. A plurality of apertures 84, preferably eight apertures, are defined in the main portion 76 extending between the recess 72 and an underside of the main portion 76. The apertures 84 permit fluid to flow from the underside of the stop member 70 and into the recess 72 during a compression cycle as described below. One or more recesses 86 may be defined in an upper surface of the insert 80 to act as gripping surfaces for threading the insert 80 through the hole 78.

An alternative stop member 70' is shown in FIGS. 11–13. The stop member 70' is similar to stop member 70 except that the main portion 76' does not define a hole nor include an adjustable insert. Instead, the main portion 76' includes a substantially planar lower surface 82'. Either or both of the stop members 70 or 70' may be used in the cell culture compression assembly 2.

Figure 15:
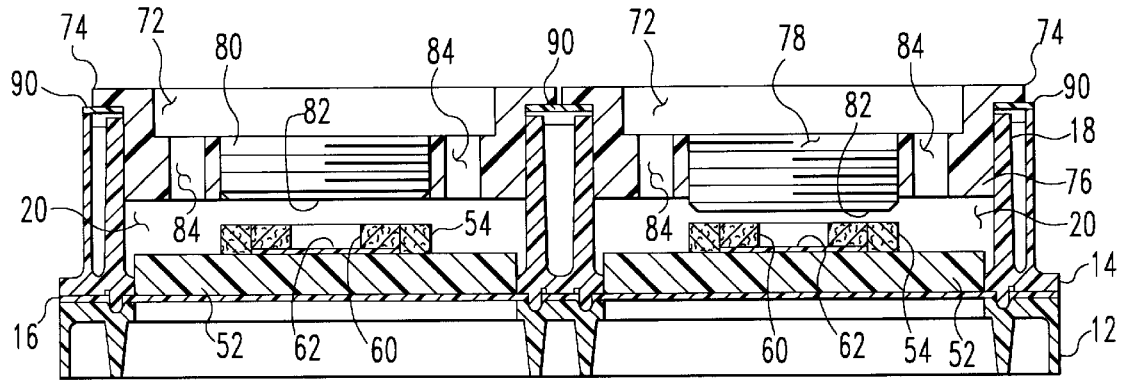
FIG. 15 is a cross-section taken along lines XV—XV in FIG. 2 and showing the sample support member and the stop member in an assembled relationship.
Figure 16:
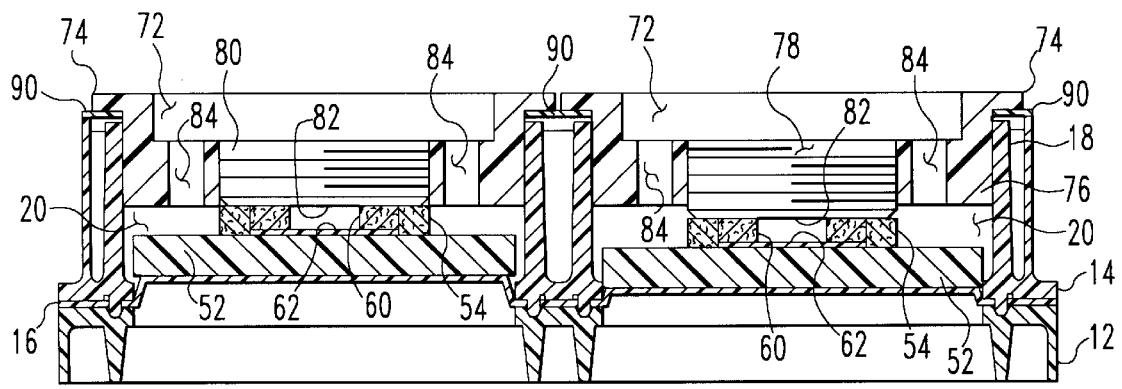
FIG. 16 is a cross-section, similar to FIG. 15, showing the cell culture plate and stop member upon application of positive pressure to the underside of the membrane.

Preferably, as shown in FIGS. 1, 15, and 16, a shim 90 is positioned between the cell culture plate 10 and the flange 74. The shim 90 defines a plurality of openings 92 aligned with the wells 20 of the cell culture plate 10. The shim 90 seats on top of the walls 18 of the wells 20 of the cell culture plate 10. The stop members 70 are fitted into the wells 20 of the cell culture plate 10 such that the flanges 74 seat on the shim 90 and the main portions 76 extend into the wells 20. Alternatively, the shim can be eliminated and the flanges 74 of the stop member 70 can be seated directly onto the walls 18 of the cell culture plate 10.

FIGS. 15 and 16 show the assembled relationship of the cell culture plate 10, sample support members 50, stop members 70, and shim 90. In the left-hand side of FIG. 15, the lower surface 82 of the insert 80 of the stop member 70 is flush with the underside of the main portion 76. The right side of FIG. 15 shows the insert 80 threaded downwardly so that the lower surface 82 thereof extends further down into the well 20 than the underside of the main portion 76 of the stop member 70. FIG. 16 shows the position of the membrane 16 with the sample support member 50 attached thereto upon application of positive pressure to the underside of the membrane 16. The membrane 16 and the sample support members 50 are urged upwardly in the direction of the stop members 70. When this occurs, the sample support member 50 is compressed against the lower surface 82 of the insert 80 of the stop member 70. When the retaining member 54 and the sample holder 60 are formed from a compressible material, they do not shield a cell culture contained within the sample holder from compression. Preferably, the sample holder 60 and the retaining member 54 are compressible to about five millimeters in height.

The cell culture compression assembly 2 is used to apply compressive forces (load) to cultured cells by delivering compressed air to the underside of the membrane 16. The pressure from the compressed air forces the membrane 16 to flex upwardly as shown in FIG. 16. The sample support member 50, containing a sample of cultured cells, is moved upwardly until the sample support member 50 abuts the stop member 70 and the retaining member 54 and the sample holder 60 are compressed against the stop member 70. When the membrane 16 moves upwardly, the volume of space between the membrane 16 and the stop member 70 is reduced. Fluid present in that space is forced out through the apertures 84 into the recess 72. The amount of compressive load applied to cells retained in the sample chamber(s) of the sample holder 60 is controlled by regulating the air pressure to the underside of the membranes of the cell culture plates. Preferably, compressed air is delivered to the underside of the membrane 16 in waves or pulses with a relaxation period when the membrane 16 and sample support member 50 move downwardly away from the stop member 70 in between compression periods of applied pressure to mimic the repetitive compressive loading applied to cells in vivo. During the relaxation period, fluid which flowed into the recess 72 during the compression period flows in the opposite direction back into the space between the membrane 16 and the stop member 70.

The rate of rise (strain rate) of the membrane, duration of the load, and the amount of force applied to the cells is controllable by regulating the shape of the wave form of the applied pressure. The number of cycles of pressure pulses or the total duration of cyclic load and rest periods applied to the cell cultures may all be varied and controlled to impart different compressive loading to the cultured cells. In addition, shims (not shown) can be placed in the cell culture well 20 to limit the distance that the sample support member travels to a defined distance such as five, ten, or fifteen percent of the height of the sample chamber. The force applied to the sample is regulated by valves controlled by specialty software, such as FLEXSOFT™ in a FLEXER-CELL STRAIN UNIT® available from Flexcell International Corporation of McKeesport, Pa.

Figure 20:
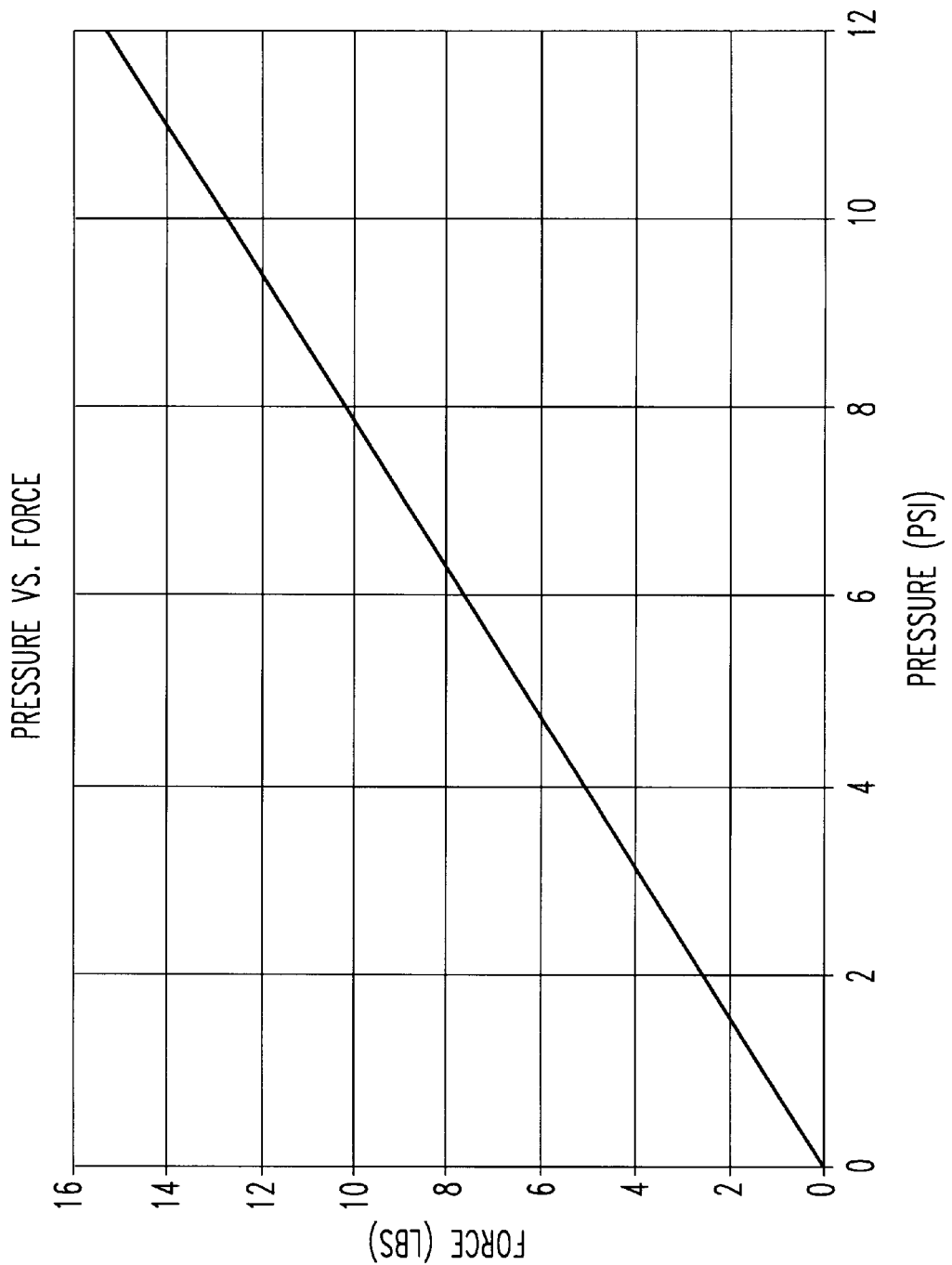
FIG. 20 is a graph of the force versus pressure which results upon applying pressure to the underside of the membrane.

It has been found that the pressure applied by the cell culture compression assembly 2 is linear with respect to the force applied to cells contained therein. FIG. 20 is a graph of force delivered to the cells in pounds (lbs.) versus applied pressure in pounds per square inch (psi) when using the cell culture compression assembly 2. The cell culture compression assembly 2 can be used to condition explants of cartilage to withstand the rigors of the in vivo environment in a joint. The cell culture compression assembly 2 can also be used to study the effect of varying the level of compressive load on cultured cells.

Figure 14:
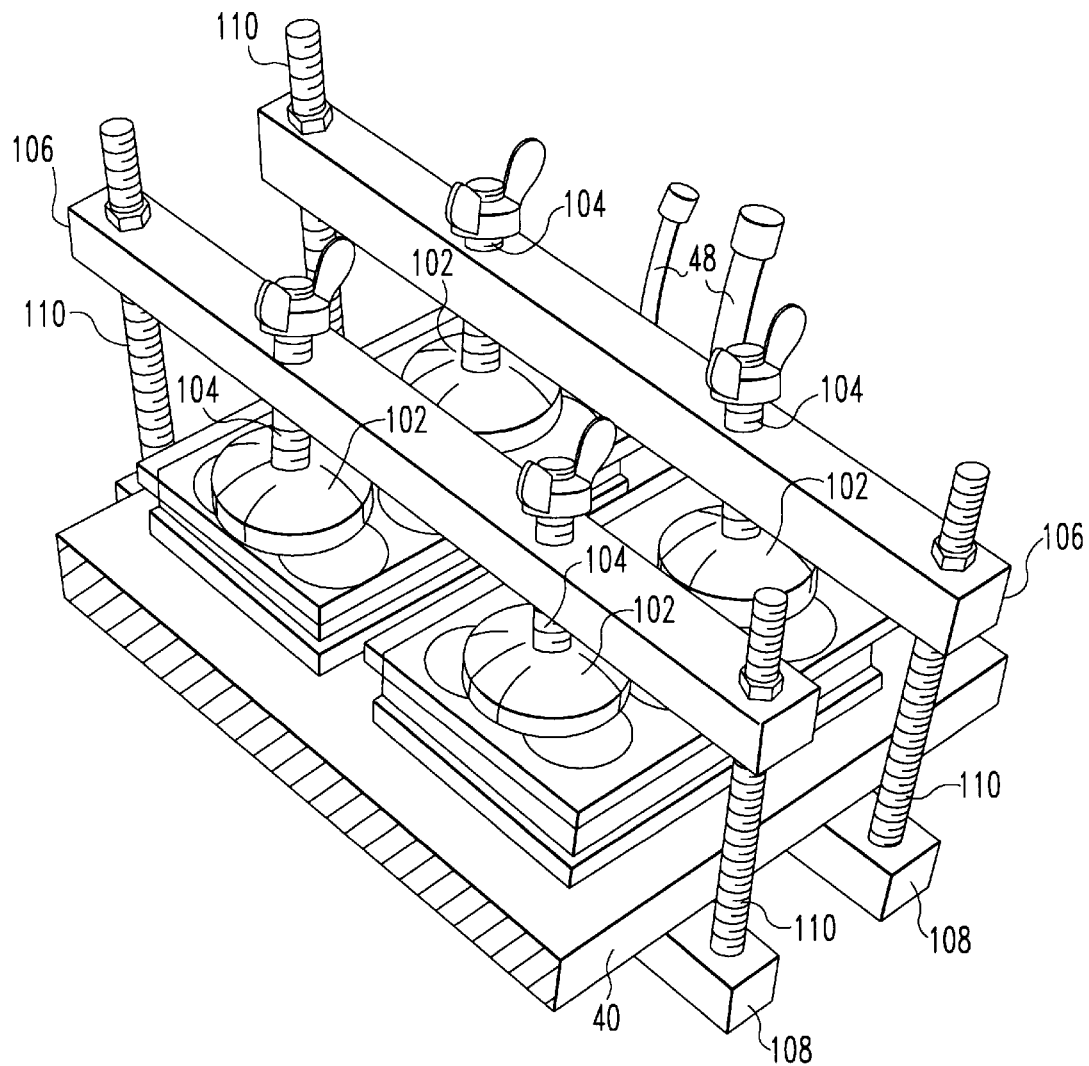
FIG. 14 is a perspective view of a portion of the cell culture base plate with gasket and two of the cell culture plates, shim, and stop members shown in FIG. 1 clamped together in an assembled relationship.

Pressure may be applied to the underside of the membranes by any mechanism capable of delivering a fluid, preferably compressed air, thereto. One such mechanism is shown in FIG. 1 and shown schematically in FIG. 14 which indicates the assembled relationship of the cell culture plate 10 and shim 90 with gasket 30 and baseplate 40. For simplicity, the stop members 70 are not shown in FIG. 14 in order to show the basic structure of the cell culture compression assembly 2 in conjunction with a pressure source. The cell culture base plate 40 includes recessed portions 42, shown in FIG. 1, each being adapted to receive the gasket 30 and the cell culture plate 10. A bottom of each of the recessed portions 42 defines an opening 44. The openings 44 communicate with a passageway (not shown) defined in the base plate 40 with ports 46 which are connected to a source of pressure via pressure lines 48 shown in FIG. 14. A clamping mechanism 100 clamps together the base plate 40, gasket 30, cell culture plates 10, shims 90, and stop members 70 (not shown). The clamping mechanism 100 includes a plurality of disk-shaped pads 102 positioned over and partially covering the wells 20. The pads 102 are fixed to threaded vertical rods 104 which are suspended from upper horizontal beams 106. Lower horizontal beams 108 positioned on the underside of the base plate 40 are clamped to the upper horizontal beams 106 via threaded clamping rods 110. The rods 104 and 110 are connected to the beams 106 and 108 via conventional fasteners such as hex nuts or wing nuts. Upon assembly of the clamping mechanism 100, the pads 102 urge the stop members 70 and shim 90 against the cell culture plate 10. Clamping mechanism 100 is meant to be exemplary only. A variety of other clamping mechanisms can be used to retain the stop members 70 seated on the shim 90 or cell culture plate 10.

Figure 17:
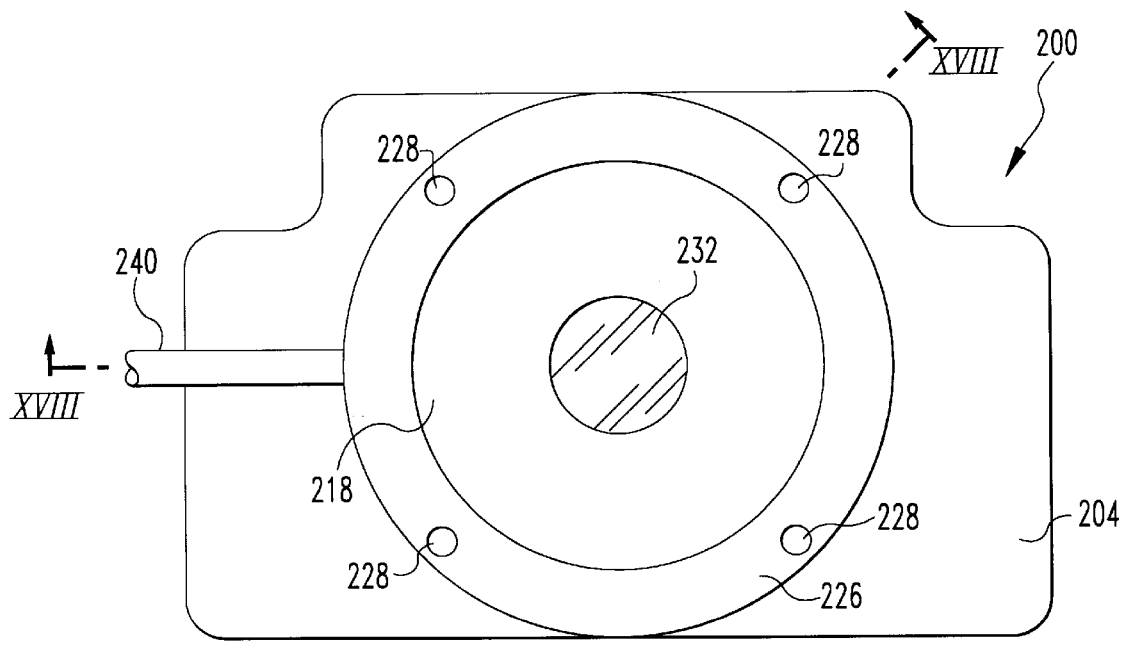
FIG. 17 is a top view of an alternative cell culture compression assembly using a single well cell culture plate.
Figure 18:
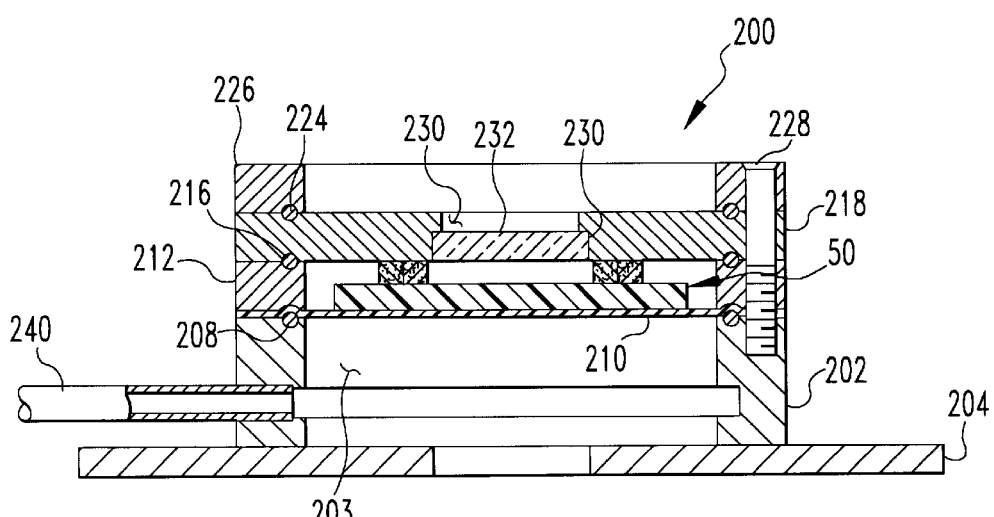
FIG. 18 is a cross-section taken along lines XVIII—XVIII in FIG. 17.
Figure 19:
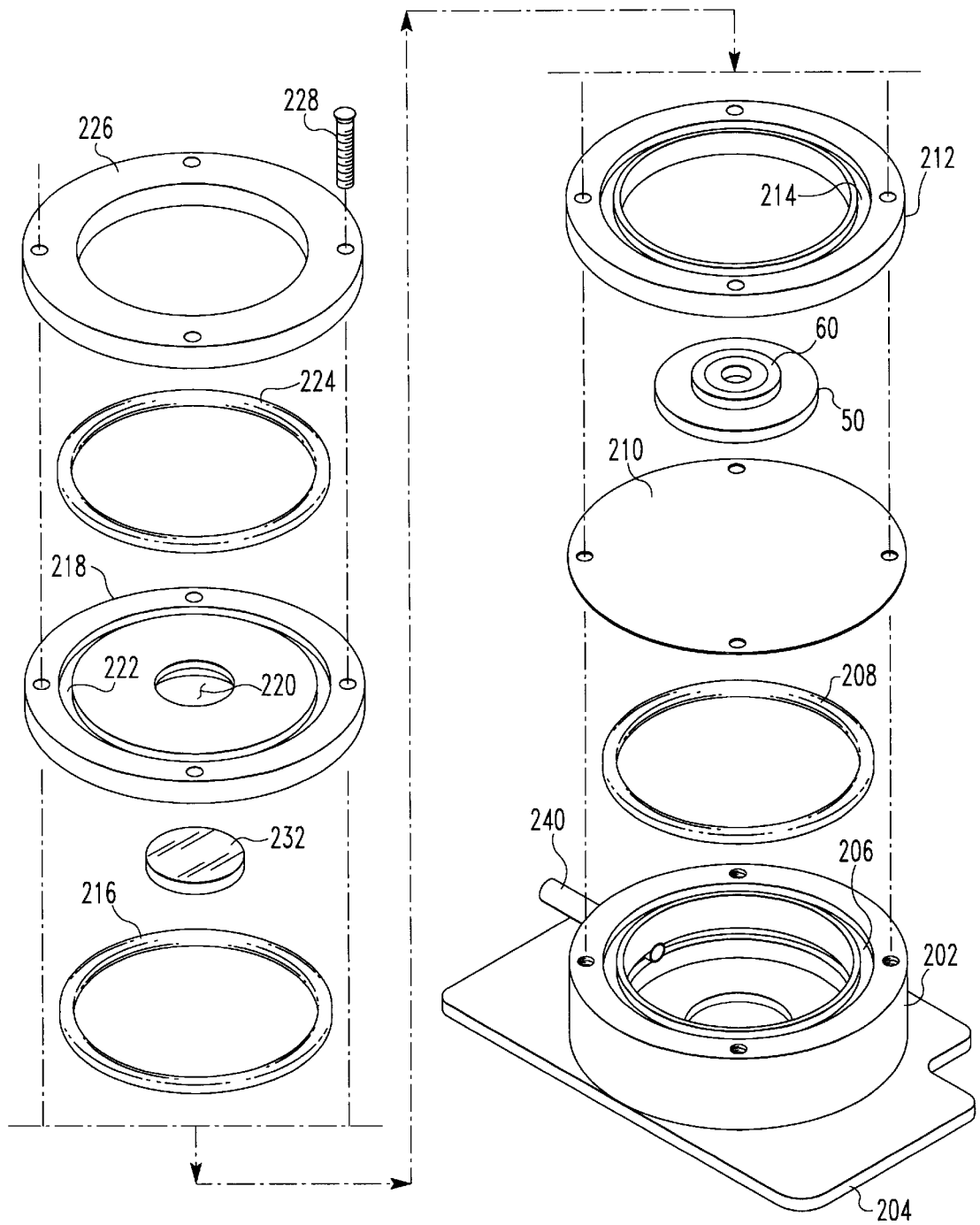
FIG. 19 is an exploded perspective view of the cell culture compression assembly shown in FIG. 18.

The cell culture compression assembly 2 described above incorporates a multi-well cell culture plate. Alternatively, as shown in FIGS. 17–19, the present invention further includes a single-well cell culture compression assembly 200. The cell culture compression assembly 200 is similar to the cell culture compression assembly 2 in the use of a cell culture plate having a flexible membrane to which is fixed the sample support member 50.

The cell culture compression assembly 200 shown in FIGS. 17–19 includes a cylindrical body 202 defining a well 203. The body 202 is fixed to a plate 204 that fits a stage micrometer that holds the cell culture compression assembly 200 to the stage. A circular groove 206 is defined in the top planar surface of the body 202 and is sized to accept a sealing gasket 208. A flexible membrane 210 is positioned over the top surface of the body 202 and is covered with a ring-shaped plate 212. A sample support member 50 as described above with respect to cell culture compression assembly 2 is fixed to the membrane 210. The top surface of the ring-shaped plate 212 also defines a groove 214 which is sized to accept a sealing gasket 216. A stop member 218 defining a bore 220 is positioned over the ring-shaped plate 212. The stop member 218 defines a circular groove 222 which is sized to accept a sealing gasket 224. A clamping ring-shaped plate 226 is positioned over the stop member 218. A plurality of fasteners 228 (only one being shown in FIG. 19), such as screws, are mounted about the perimeter of the cell culture compression assembly 200 and engage mating holes defined through the respective components. The bore 220 in the stop member 218 includes an enlarged portion 230 which is sized to accept a transparent window 232, preferably formed of glass. A pressure differential supply line 240 extends through the side of the cylindrical body 202 and opens into the well 203 so that a pressurized fluid may be exerted on the underside of the membrane 210.

The cell culture compression assembly 200 is operated in a similar manner to and has the same uses as the multi-well cell culture compression assembly 2 described above. A source of pressure such as compressed air is delivered through the supply line 240, into the well 203 and exerts pressure on the underside of the flexible membrane 210. The flexible membrane 210 moves upwardly in response to the pressure in the well 203 and urges the sample support member 50 into compression with the underside of the transparent window 232. The source of pressure may be regulated to induce repeated compressive loadings upon cells contained in the sample holder 60.

Although the present invention has been described in connection with a multi-well cell culture plate and a single-well cell culture plate, the compression assembly of the present invention may be used with any enclosure having a wall and a base where the base includes a flexible membrane which can be flexed upwardly to induce compression between a stop member and a sample support member. The wells of the cell culture compression assemblies described above have been described as having a generally cylindrical shape. Again, this is only a matter of choice and the shape of the enclosure of the cell culture compression assembly may be any variety of designs as the need arises.

It will be readily appreciated by those skilled in the art that modifications may be made to the invention without departing from the concepts disclosed in the foregoing description. Such modifications are to be considered as included within the following claims unless the claims, by their language, expressly state otherwise. Accordingly, the particular embodiments described in detail herein are illustrative only and are not limiting to the scope of the invention which is to be given the full breadth of the appended claims and any and all equivalents thereof.

I claim:

1. A cell culture compression assembly comprising:
    an enclosure comprising a wall and a base, said base comprising a flexible membrane;
    a sample support member positioned on said membrane; and
    a stop member mounted on said wall in overlying spaced apart relationship to said sample support member, wherein said membrane is configured to flex towards said stop member thereby compressing said sample support member against said stop member.

2. The cell culture compression assembly as claimed in claim 1 wherein said stop member comprises a flange surrounding a main portion, said flange being seated on said wall.

3. The assembly as claimed in claim 2 wherein said stop member main portion includes a lower surface, wherein a position of said lower surface is adjustable.

4. The assembly as claimed in claim 3 wherein said stop member main portion defines a hole and further comprises an insert, wherein said insert includes said lower surface and is movable through said hole.

5. The assembly as claimed in claim 4 wherein said insert is threadable into said hole.

6. The assembly as claimed in claim 1 wherein said stop member main portion defines a plurality of apertures, whereby when said membrane flexes towards said stop member, fluid present in said enclosure between said membrane and said stop member flows out of said enclosure through said apertures.

7. The assembly as claimed in claim 2 wherein said stop member main portion is made from a transparent material such that a cell culture present on the sample support member is visible through the main portion.

8. The assembly as claimed in claim 1 wherein said sample support member comprises a body and a retaining member fixed to a surface of said body, said retaining member defining an opening.

9. The assembly as claimed in claim 8 further comprising a sample holder removably positioned within said retaining member opening.

10. The assembly as claimed in claim 9 wherein said sample holder comprises a cell culture sheet and a holder body fixed to one side of said sheet, said holder body defining at least one sample chamber, the other side of said sheet being removably positioned on said body in said opening of said retaining member.

11. The assembly as claimed in claim 10 wherein said retaining member comprises a first ring and said holder body comprises a second ring.

12. The assembly as claimed in claim 10 wherein said holder body comprises a disk-shaped member defining a plurality of sample chambers.

13. The assembly as claimed in claim 8 wherein said retaining member is compressible to a height of about five millimeters above said surface of said body.

14. A cell culture compression assembly comprising:
    a cell culture plate defining an opening and having a flexible membrane covering said opening;
    a sample support member positioned on said membrane; and
    a stop member positioned in overlying spaced apart relationship to said sample support member, said membrane being configured to flex towards said stop member, thereby compressing said sample support member against said stop member.

15. The assembly as claimed in claim 14 wherein said cell culture plate includes a wall surrounding said membrane thereby defining a cell culture well, and wherein said stop member comprises a flange portion and a main portion, said flange portion being seated on said wall.

16. The assembly as claimed in claim 15 wherein said stop member main portion extends into said well.

17. The assembly as claimed in claim 15 wherein said stop member main portion includes a lower surface, wherein a position of said lower surface is adjustable.

18. The assembly as claimed in claim 15 further comprising means for clamping said stop member against said walls.

19. The assembly as claimed in claim 15 wherein said cell culture plate defines a plurality of openings, each said opening being covered by said flexible membrane and being surrounded by a wall thereby defining a plurality of cell culture wells, said assembly further comprising a plurality of said stop members, each said stop member being seated on one of said walls.

20. The assembly as claimed in claim 15 wherein said stop member main portion is made from a transparent material such that a cell culture present on the sample support member is visible through the main portion.

21. The assembly as claimed in claim 15 wherein said main portion defines an opening and said stop member further comprises a transparent member covering said main portion opening such that said cell culture portion is visible through the main portion opening.

22. The assembly as claimed in claim 21 wherein said wall comprises a lower member and an upper member, said membrane being fixed between the lower member and the upper member and said flange portion of said stop member being fixed to the upper member.

23. A method of applying compressive forces to cultured cells comprising the steps of:
    a) providing a flexible membrane;
    b) positioning a sample support member containing a cell culture on the flexible membrane;
    c) positioning a stop member in overlying spaced apart relationship to the sample support member; and
    d) flexing the membrane in the direction of the stop member thereby compressing the cell culture against the stop member.

24. The method as claimed in claim 23 further comprising the steps of:
    e) allowing the membrane to relax; and
    f) repeating steps d) and e).

25. The method as claimed in claim 24 wherein the sample support member comprises a body and a retaining member fixed to one side of the body, such that the retaining member contains the cell culture, and wherein said step of flexing the membrane compresses the retaining member to a height of about five millimeters above the surface of the body.

26. The method as claimed in claim 25 wherein the membrane is incorporated into a cell culture plate defining an opening with the membrane covering the cell opening, the opening surrounded by a wall thereby defining a well, and wherein the stop member is positioned on the wall.

27. The method as claimed in claim 26 wherein the stop member extends into the well at an adjustable distance, such that the pressure exerted on the cell culture during said step of flexing the membrane is variable.

* * * * *